US005868690A

United States Patent [19]
Eischen, Sr.

[11] Patent Number: 5,868,690

[45] Date of Patent: Feb. 9, 1999

[54] INFLATABLE BOOT AND METHOD FOR ITS MANUFACTURE

[76] Inventor: Clement G. Eischen, Sr., 1232 SE. 282nd Ave., Gresham, Oreg. 97080

[21] Appl. No.: 850,751

[22] Filed: Apr. 30, 1997

[51] Int. Cl.[6] .............................. A61H 9/00; A61F 5/058

[52] U.S. Cl. ............................ 601/151; 601/152; 601/15; 128/DIG. 20; 602/13; 602/14

[58] Field of Search .................................... 601/148–152, 601/55, 27, 15; 606/202; 128/DIG. 20; 602/13, 14, 2

[56] References Cited

U.S. PATENT DOCUMENTS

| | | | |
|---|---|---|---|
| 1,257,086 | 2/1918 | Marcellus . | |
| 2,531,074 | 11/1950 | Miller . | |
| 2,694,395 | 11/1954 | Brown . | |
| 3,083,708 | 4/1963 | Gottfried . | |
| 3,351,055 | 11/1967 | Gottfried | 602/13 |
| 3,403,673 | 10/1968 | MacLeod . | |
| 3,469,576 | 9/1969 | Smith et al. . | |
| 3,548,809 | 12/1970 | Conti . | |
| 3,824,992 | 7/1974 | Nicholson et al. . | |
| 3,888,242 | 6/1975 | Harris et al. . | |
| 4,067,063 | 1/1978 | Ettinger . | |
| 4,128,951 | 12/1978 | Tansill . | |
| 4,166,460 | 9/1979 | Applegate . | |
| 4,227,320 | 10/1980 | Borgeas . | |
| 4,263,905 | 4/1981 | Couch . | |
| 4,266,298 | 5/1981 | Graziano . | |
| 4,370,975 | 2/1983 | Wright . | |
| 4,502,470 | 3/1985 | Kiser et al. . | |
| 4,722,332 | 2/1988 | Saggers | 128/DIG. 20 |
| 4,805,601 | 2/1989 | Eischen . | |
| 4,922,893 | 5/1990 | Wright et al. . | |
| 4,947,834 | 8/1990 | Kartheus et al. . | |
| 4,977,891 | 12/1990 | Grim . | |
| 5,113,599 | 5/1992 | Cohen et al. . | |
| 5,343,638 | 9/1994 | Legassie . | |
| 5,348,530 | 9/1994 | Grim et al. . | |
| 5,376,130 | 12/1994 | Courtney . | |
| 5,415,624 | 5/1995 | Williams | 602/2 X |
| 5,435,009 | 7/1995 | Schild et al. | 128/DIG. 20 |

FOREIGN PATENT DOCUMENTS

| | | | |
|---|---|---|---|
| 960537 | 1/1975 | Canada . | |
| 0039629 A1 | 11/1981 | European Pat. Off. . | |
| 2737734 A | 12/1978 | Germany . | |
| 260822 | 5/1970 | Russian Federation . | |
| 574213 | 10/1977 | Russian Federation . | |
| 1171361 | 11/1969 | United Kingdom | 128/DIG. 20 |

*Primary Examiner*—Danton D. DeMille
*Attorney, Agent, or Firm*—Kolisch Hartwell Dickinson McCormack & Heuser

[57] ABSTRACT

An inflatable boot and method for its manufacture, in which the boot includes a bladder for encasing at least a portion of a human foot and at least a portion of an ankle. The bladder is defined by an inner and an outer layer of substantially gas-tight material, and includes fluidically interconnected wall and sole portions. The wall portions are sized and shaped for collectively encasing a human ankle and the sole portion is sized and shaped for encasing a sole of a human foot. A structural interconnection joins the inner layer of the bladder substantially directly to the outer layer at a location interposed the sole portion and one of the wall portions to create a foot-supporting contour for the sole portion of the bladder when the bladder is inflated. The bladder for the boot is manufactured in a flattened condition, and then folded over and joined at seams to define a boot.

22 Claims, 4 Drawing Sheets

INFLATABLE BOOT AND METHOD FOR ITS MANUFACTURE

BACKGROUND OF THE INVENTION

The present invention relates generally to devices for the rehabilitation of injuries, and particularly to an improved inflatable boot for wearing by an individual to promote healing of an injured foot, ankle or lower leg area. An inflatable boot is a therapeutic device worn on an injured foot and ankle to encase and massage the injured area, and to create an increase and decrease of pressure within the muscles of the foot and lower leg to simulate the pressure changes normally experienced during walking. These pressure changes are important to the flow of blood through the foot and lower leg. My earlier U.S. Pat. No. 4,805,601, incorporated herein by reference, discusses one such inflatable boot. The present device offers many advantages over my earlier device, such as being easier to manufacture and use.

The increase and decrease of pressure within the muscles of the foot and lower leg improves blood flow by acting as the driving force of a naturally occurring pump within the foot and lower leg. The veins of the foot and lower leg contain one-way check valves. When the pressure in the muscles and tissues surrounding the veins is increased, blood is forced out of the veins toward the heart, and when the pressure decreases, fresh blood is allowed to flow into the veins. Repeated increases and decreases of pressure, such as when walking, therefore operate to pump blood through the foot and lower leg. This pumping action is particularly important for the return of blood to the heart from the foot and lower leg because these portions of the human body are a long way from the heart.

When a foot is injured, it often is painful and harmful to put weight or the foot, or even to flex the muscles of the foot. It therefore is very difficult to maintain a proper flow of blood through the injured foot. A proper flow of blood is helpful to recovery of the injured area because blood is essential to the functioning of the cells in the body.

It has been found that one safe way to improve the flow of blood within an injured foot is to encase the foot and injured area in an inflatable bladder, as described briefly above. The pressure within the bladder then is increased and decreased to result in an increase and decrease of pressure on the tissues of the foot. A pressure change within the bladder may be controlled by a pump and valve attached to the bladder, or by pressing on and releasing the exterior of the bladder.

A simple way of pressing on the exterior of a bladder is for the wearer of the bladder to press the bladder against a wall, floor, bed frame, or other obstacle. The boot shape of the bladder of the present invention includes a sole portion corresponding to the sole of an encased foot, and allows a pressure change to be controlled by pressing on and releasing the sole portion of the foot. This is a movement that is particularly easy for an injured wearer of the boot to make, because it takes advantage of the large muscles of the leg that are used for walking. The sole portion of the bladder is fluidically interconnected to a leg portion, by which it is meant that a pressure change in fluid within the sole portion effects an immediate, corresponding pressure change in fluid within the leg portion. In this manner, an injury located anywhere within the area encompassed by the boot may be operated upon by a pressure change in the boot, and may receive fill benefit of the pumping action described.

Inflatable boots are used to treat various types of injuries, including bruises, sprains, fractures, torn muscles, and injured tendons. For most of these injuries, the orientation of the injured foot within the boot is very important. The boot must protect the injured foot and lower leg, prevent excessive motion of the foot about the ankle, and include a sole portion that is of a sufficient volume so that pressing on the sole portion produces a desirable increase in pressure within the bladder surrounding the foot, preferably from approximately 1-psi to 2-psi.

An inflatable boot provides protection by maintaining a cushion of slightly pressurized air around the foot and lower leg, at a pressure of approximately 1-psi when the boot is in its relaxed condition. A thick cushion usually provides better protection than a thin one. The pressure within the cushion tends to force the walls of the cushion into a stable configuration, at least partially immobilizing the foot to limit motion about the ankle. A thick cushion within the sole portion of the boot also means that the sole portion is of a relatively large volume, allowing a substantial increase of pressure within the sole portion with a simple pressing force applied to the sole portion. For the preferred embodiment, the pressure within the boot may be increased from 1-psi when relaxed to 2-psi when a pressing force is applied to the sole portion. If adequate interconnection is provided between the sole portion and the rest of the boot, an increase of pressure in the sole portion results in the desired increase in pressure within the entire bladder of the boot.

The importance of each of these factors varies depending on the condition of the wearer of the boot. For a relatively immobilized wearer, such as someone suffering from injuries in addition to those of the foot, none of the factors is particularly important. The foot will not be subjected to many dangers that would require protection and support, and the boot may be used with an external pressure source like a pump. As the wearer becomes more mobile, protection and support become more important, and utilization of the self-powered method of pressure increase becomes more viable.

After careful study of all of the issues identified above, I have found that the effectiveness of an inflatable boot is a function of how accurately the boot may be placed on the foot, how thick of an air cushion is provided around the foot for protection, how positively the sole of the foot may be located on a fluid-filled platform within the boot, and how effectively pressure is transmitted from a sole portion of the boot underlying the sole of the foot to wall portions, surrounding the ankle and lower leg. The present invention includes elements that satisfy each of these design parameters. The preferred embodiment includes both visual and tactile indicators of the proper placement of the boot, in the form of notches near a heel region of the boot corresponding generally to the bottom of the heel of the foot, regions of noninflation near the sole portion of the boot generally along lines that correspond to the proper placement of the sole of the foot, and a partially enclosed toe region that corresponds generally to the proper placement of the top of the toes of the foot. It also includes a structure that causes the boot to form a foot-supporting platform under the sole of the foot when the boot is inflated. The structure also defines a sole portion and connected wall portions with fluid transfer between the sole portion and the wall portions being facilitated by a relatively unobstructed interior. Alternatively, a sling may be suspended within the boot to provide a platform for both locating and supporting the foot. The construction of the preferred and alternative embodiments is relatively simple, allowing the production of a cost-effective therapeutic device.

The inflatable boot of my earlier patent fulfilled all of the design requirements identified above, but only because the boot of my earlier patent is a relatively complicated structure, with separately defined sole and wall portions interconnected by a series of openings or apertures. A resulting drawback of that structure is that it is difficult to manufacture, and therefore relatively expensive. This drawback is solved by the novel construction of the present invention.

In addition to my earlier patent, several other patents show examples of inflatable boots. For example, U.S. Pat. Nos. 3,083,708 and 3,403,673, incorporated herein by reference, each show what is believed to be an inflatable boot formed with one or two chambers that have a substantially unobstructed interior. The boots disclosed in U.S. Pat. Nos. 3,083,708 and 3,403,673 also appear to be relatively simple in construction, and therefore easy to manufacture.

However, each of these two devices is formed with a seam that extends along the center of the sole portion of the boot, creating a valley that may limit the volume of the sole portion when inflated. This may limit the effective increase in pressure that is affected by pressing on the sole portion. The boot of my present invention may be made from a folded-over bladder that eliminates the center seam of these prior devices, as described in more detail below. The other benefits of my invention, as described herein, may be used with boots that include such a center seam, and these alternative constructions of boots are intended to be encompassed within the spirit and scope of the invention defined in some of the appended claims.

More complicated inflatable boots are found in U.S. Pat. Nos. 3,824,992, and 3,888,242, also incorporated herein by reference. As with the above-discussed patents, these boots are manufactured with what appears to be a single bladder having a relatively unobstructed interior. The '992 device includes a relatively stiff outer cover, and the '242 device includes numerous seams and overlapping flaps. Both of these features may complicate manufacture and use of inflatable boots, but may be used as part of alternative embodiments also within the spirit and scope of the invention defined in the appended claims.

The treatment of foot and lower leg injuries may involve the application of cold or heat to the injured area, such as by placing an ice pack or a heat pack on the injured area. Ice packs and heat packs are examples of what are referred to more broadly herein as thermal treatment devices. Proper placement of thermal treatment devices is very important, and often very difficult, because of the numerous possible locations of the varied injuries for which inflatable boots are used.

For many foot injuries, the application of a thermal treatment device under slight pressure, such as the 1- to 2-psi found within an inflatable boot, may be beneficial because it increases the thermal transfer rate between the treatment device and the injured area to be treated. The increase and decrease of pressure provided by proper use of an inflatable boot also helps to reduce the discomfort of a treatment device pressing against the foot, and to maintain the blood flow that otherwise would be restricted further by the treatment device. The preferred embodiment of the present invention includes a pocket formed on the inner, foot-contacting portion of the boot that aids in proper placement of a thermal treatment device on the foot, and allows the beneficial increases and decreases of pressure on the foot to be transmitted through the treatment device.

It is a general object of the present invention to provide an inflatable boot that is easy to manufacture and simple to use.

It is another object of the invention to provide an inflatable boot with a bladder, and with a structural interconnection joining an inner layer of the bladder to an outer layer of the bladder to create a foot-supporting contour when the bladder is inflated.

A still further object of the invention is to provide an inflatable boot with a visual reference indicating the proper placement of a heel of a human foot, prior to inflating the boot, so that an inflated cushion may form properly under the sole of the foot when the boot is inflated.

It is an additional object of the invention to provide an inflatable boot with a platform-defining sling so that the sling may support a human foot that is inserted into the boot.

A still further object of the invention is to provide an inflatable boot with a pocket in which a thermal treatment device may be held.

These and additional objects and advantages of the present invention will be understood more readily after a consideration of the drawings and the detailed description of the preferred embodiment.

DETAILED DESCRIPTION OF THE INVENTION

Figures 1, 2, 3, 4:
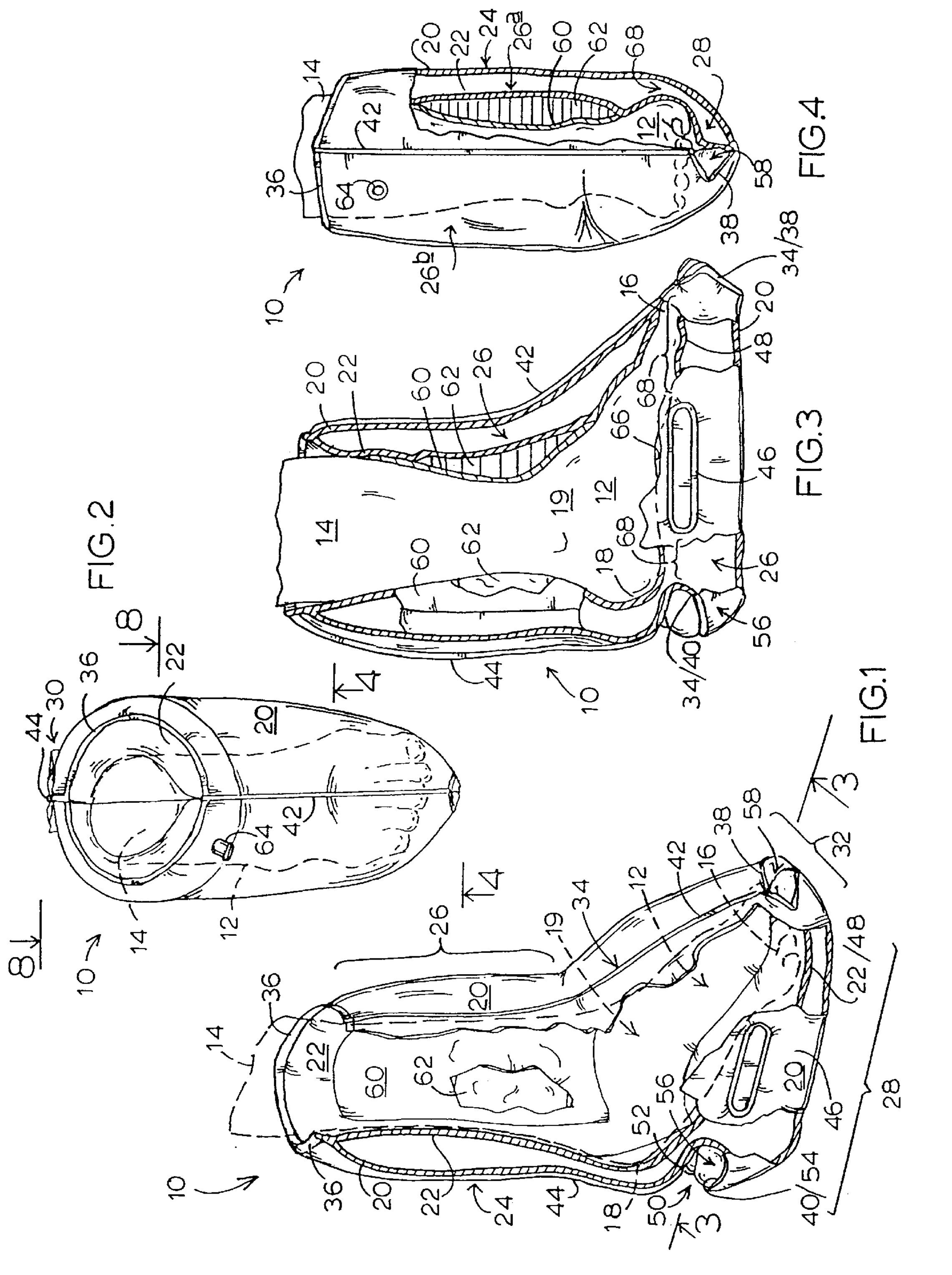
FIG. 1 is an isometric view of the preferred embodiment of the boot of the present invention, taken generally from the top, front, and right of the boot, with the boot being fragmented to show various hidden details, a right foot being shown in the boot, and the boot shown in its inflated but relaxed condition.
FIG. 2 is a plan view of the top of the boot shown in FIG. 1, with line 1—1 indicating generally the line along which the boot is fragmented in FIG. 1.
FIG. 3 is an elevation of the right side of the boot shown in FIG. 1, fragmented approximately as shown in FIG. 1, along line 1—1 of FIG. 2.
FIG. 4 is an elevation of the front of the boot shown in FIG. 1, fragmented generally along line 4—4 of FIG. 2 to expose interior details of the left side of the boot.

The preferred embodiment of the boot of the present invention is shown in FIG. 1, indicated generally at 10. Boot 10 is shown being worn on a human foot 12 and a lower leg 14, including toes 16, a heel 18, and an ankle 19. Boot 10 includes a cover or outer layer 20 joined or sealed to a liner or inner layer 22. Cover 20 and liner 22 preferably each are made from a single, contiguous sheet of flexible gas-tight material. Coated nylon cloth, such as 200 denier nylon oxford, has been found to work particularly well for cover 20 because it is lightweight, easy to work with, and wear-resistant. Ether-based polyurethane, approximately 0.012-inch thick, works well for liner 22 because it is inexpensive, durable, easily sealed, and generally non-irritating to an inserted human foot.

Cover 20 and liner 22 collectively define a bladder 24 for boot 10. Boot 10 may be inflated by blowing or pumping air or other fluid into bladder 24. Bladder 24 preferably is contiguous, so that a pressure change within any part of bladder 24 may be communicated to the rest of bladder 24, when bladder 24 is inflated.

Bladder 24, and more specifically portions of cover 20 and liner 22, is shaped to form boot 10. Bladder 24 defines an inflatable leg portion indicated generally at 26, and an inflatable sole portion indicated generally at 28. Leg portion 26 is sized and shaped for encasing at least a portion of lower leg 14, such as ankle 19, and sole portion 28 is contiguous with leg portion 26, for encasing at least a portion of foot 12. For reference, a heel region 30 and a toe region 32 of boot 10 also are identified in FIG. 1.

An understanding of the joining of cover 20 to liner 22, and of the joining of the resulting bladder 24 to itself, is important to an understanding of the benefits of the present invention. The joining of the two sheets of material is done using conventional radio frequency sealing or heat sealing, resulting in a bladder seal 34. Several identifiable segments of bladder seal 34 are visible in FIG. 1, including a pair of top seals 36, a toe seal 38, and a heel seal 40. Most of top seal 36 of the right side of boot 10 is not shown in the fragmentary view of FIG. 1.

Seam segments of bladder seal 34 are interconnected directly to matching seam segments of seal 34 to create both a front seam 42 and a rear seam 44. As used herein, the term "seam" differs slightly from the term "seal." A seam is the joining of two portions of bladder 24 to define a boot, while a seal is the simple joining of cover 20 to liner 22 to define a bladder. It is the seams that hold bladder 24 in a foot-encasing boot shape, and the seals that hold fluid within bladder 24.

In the preferred method, described below, all of the seals are formed before the seams are formed. It is possible, however, to form the seal concurrently with the seams, so that, in essence, the seams are the seal in those portions of the bladder. It also is possible to make boot 10 out of a single piece of material, by molding or extruding material, for example. These alternative constructions of boot 10 are intended to be encompassed within the spirit and scope of the invention defined in some of the appended claims.

A further aspect of the preferred embodiment that is visible in FIG. 1 is what might be thought of as an island seal 46, because it preferably is substantially separate from bladder seal 34. Island seal 46 may be described alternatively as a structural interconnection because it joins or interconnects cover 20 directly to liner 22, preferably at a location on an external surface of bladder 24 interposed sole portion 28 and leg portion 26, intermediate front seam 42 and rear seam 44, and independent of bladder seal 34. A first structural interconnection 46 is formed on the right side of boot 10, visible in FIG. 1, and an opposing, separate, second structural interconnection is formed on the left side of boot 10, mostly hidden in FIG. 1. Structural interconnection 46 also may be described with respect to its effect on the inflation of bladder 24, in which case it is identified as region of noninflation 46.

The geometrical configuration of structural interconnection 46 may vary depending on the choice of materials for cover 20 and liner 22, and on the desired ornamental appearance for boot 10. The elongated oval shown in FIG. 1 for structural interconnection 46 provides a joining of cover 20 to liner 22 that is of sufficient strength, and that does not contain any force-concentrating corners that might lead to material failure or delamination. However, other geometrical configurations, for example, a series of island seals in a row or simply a linear seal may be used, if desired.

By joining cover 20 and liner 22 in a region within the interior of bladder 24, between leg portion 26 and sole portion 28, structural interconnection 46 creates a foot-supporting contour for sole portion 28 of bladder 24, causing a fluid-filled inflated cushion to form under foot 12 when bladder 24 is inflated, as shown in FIG. 1. Thus, liner 22 within sole portion 28 forms a platform 48 for the foot when bladder 24 is inflated.

Still referring to FIG. 1, the formation of platform 48 under foot 12 is defined as well by inwardly extending notches 50 included in the periphery of bladder 24, only one of which is seen in FIG. 1 on the right side of boot 10, within heel region 30. Each notch 50 is included in both cover 20 and liner 22, and generally extends along bladder seal 34, with an upper seam portion 52 being a lower end of rear seam 44, and with a lower seal portion 54 preferably being formed independent of rear seam 44. Independently formed lower seal portions 54 create what is referred to herein as an open-looped heel for bladder 24. The heel is referred to as open-looped because bladder 24 is folded over below rear seam 44, without being closed by seam 44, although this feature is not clearly visible in FIG. 1. The inclusion of notches 50 as part of the open-looped heel allows bladder 24 to expand outwardly further immediately below heel 18 of foot 12, forming gas-filled auxiliary lobes 56 that augment the pressure-increasing volume of sole portion 28 of bladder 24.

Toe seal 38 similarly is formed independently of front seam 42, forming an open-looped toe 58 for boot 10. Open-looped toe 58 is similar to the open-looped heel of boot 10 in that a loop is formed by a portion of bladder 24 that is folded over below front seam 42, as seen in FIG. 1. The open-looped heel and open-looped toe 58 provide for some ventilation of sole portion 28, and lead to a description of inflatable sole portion 28 as open-looped as well. Structural interconnection 46 is located between heel 56 and toe 58.

Notches 50 also provide a visual reference indicating the proper placement of heel 18 of foot 12 within boot 10, prior to inflating bladder 24. Heel 18 should be held approximately aligned with notches 50. A similar visual reference is provided by structural interconnections 46, as discussed below with respect to FIG. 3. If foot 12 is properly positioned before inflation of bladder 24, an inflated cushion in sole portion 28 may form properly under foot 12 when bladder 24 is inflated.

Before leaving discussion of FIG. 1, it should be noted that boot 10 also includes a pocket 60, preferably included on or attached to liner 22. Pocket 60 facilitates the placement of an ice pack or other thermal treatment device, indicated generally at 62 in FIG. 1, adjacent an injured area. Thermal treatment device 62 may be sandwiched between bladder 24 and at least a portion of lower leg 14, ankle 19 or foot 12 that is inserted into boot 10, when bladder 24 is inflated. A matching pocket, not shown, also is included in the right side of boot 10 so that a first and second thermal treatment device such as device 62 may be placed on either or both sides of boot 10.

Referring briefly to FIG. 2, it will be seen that top seal 36 defines an opening for leg portion 14 of boot 10, through which foot 12 and lower leg 14 are inserted into boot 10. Foot 12 preferably is encased completely by boot 10, as shown. Alternatively, portions of foot 12, such as toes 16, may be exposed, such as is shown in my earlier U.S. Pat. No. 4,805,601. Cover 20, liner 22, heel region 30, toe region 32, front seam 42 and rear seam 44 are readily visible in FIG. 2. Also visible is an inlet/outlet valve 64, included in a portion of cover 20 that was cut away in FIG. 1, and therefore not visible in FIG. 1.

FIG. 3 shows more clearly the orientation of foot 12 within boot 10. Toes 16 of foot 12 are relatively near to cover 20 within toe region 32, and heel 18 of foot 12 is relatively near to notches 50, within heel region 30. The sole of foot 12, indicated generally at 66, is aligned approximately with structural interconnections 46. Again, only the right structural interconnection 46 is visible in FIG. 3.

When foot 12 is positioned within boot 10 as shown in FIG. 3, sole portion 28 is of substantial thickness. Platform 48 therefore is spaced a significant distance above the lowermost portion of cover 20 within sole portion 28. Auxiliary lobes 56, also visible in FIG. 3, augment sole portion 28. Passageways 68 remain between structural interconnection 46 and bladder seal 34 so that fluid within bladder 24 may pass easily from sole portion 28 into leg portion 26, and then back into sole portion 28. More specifically, structural interconnection 46 defines a pair of inflatable passageways fluidically connecting sole portion 28 to leg portion 26, allowing relatively unobstructed fluid flow between sole portion 28 and leg portion 26 adjacent heel region 30 and adjacent toe region 32.

Similar aspects of boot 10 are shown in FIG. 4. Front seam 42 and rear seam 44 (not visible in FIG. 4) divide leg portion 26 to form a pair of opposing leg chambers **26*a* and 26*b*, fluidically interconnected through sole portion 28 via passageways 68. Leg chambers 26*a* and 26*b* may be referred to more generally as wall portions of boot 10. The interconnection between leg chambers 26*a* and 26*b* and sole portion 28 is understood best by referring collectively to FIGS. 1, 3, and 4, in which it will be seen that the inflatable interior of bladder 24, encompassed by cover 20 and liner 22, is relatively unobstructed. Structural interconnections 46 preferably are the only obstructions within the interior of bladder 24**.

The relative proportions of leg portion 26, sole portion 28, structural interconnections 46, and, perhaps most importantly, passageways 68, as shown in the drawings, are such that an increase in pressure within any portion of bladder 24 acts almost immediately on any other portion of bladder 24. The pressure within bladder 24 is indicated visually within FIGS. 1 through 4 by the bulging of cover 20, and the fact that liner 22, pocket 60 and thermal treatment device 62 are each pressed against foot 12 and lower leg 14. The benefits of an alternating increase and decrease in pressure on foot 12 and lower leg 14 are discussed briefly above, and in more detail below, with respect to FIGS. 9 and 10.

Figure 5:
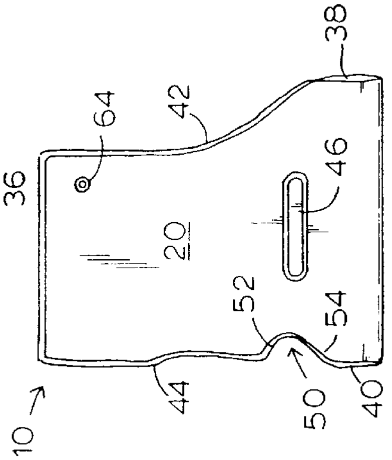
FIG. 5 is an elevation of the right side of the boot shown in FIG. 1, shown on a slightly smaller scale than in FIG. 1, shown without an inserted foot, and shown uninflated and flattened in its storage position.
Figure 6:
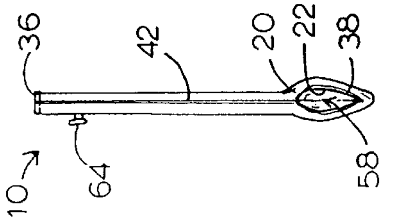
FIG. 6 is an elevation of the front of the boot shown in FIG. 5.

FIGS. 1 through 4, just discussed, show boot 10 in relation to a human foot 12. FIGS. 5 and 6, on the other hand, show boot 10 independent of a human foot. FIG. 5 shows boot 10 in an uninflated condition, mostly flattened as if for storage. Several of the elements discussed above are identified in FIG. 5. The most noticeable aspects of boot 10 in FIG. 5 include structural interconnection 46 and notches 50. FIG. 6 shows the flattened boot 10 of FIG. 5, with open-looped toe 58 shown slightly opened for clarity.

Figure 7:
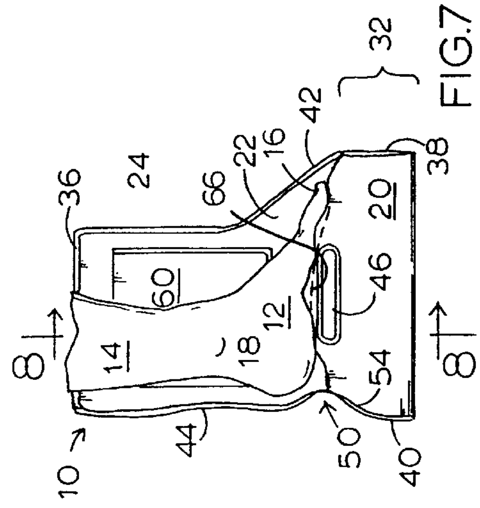
FIG. 7 is an elevation of the right side of the boot with the boot fragmented similarly to the boot shown in FIG. 3, shown on a slightly smaller scale than in FIG. 3, with a foot inserted into the boot before the boot is inflated fully.

In FIG. 7, foot 12 and lower leg 14 are shown inserted into boot 10 in a mostly uninflated condition. Toes 16 are positioned relatively close to front seam 42 in toe region 32, and heel 18 of foot 12 is positioned relatively close to notches 50. Sole 66 of foot 12 is aligned approximately with structural interconnection 46. Thus, it will be seen that foot 12 is positioned approximately as shown in FIG. 3, with respect to each of these elements of boot 10. The primary difference between FIG. 3 and FIG. 7 is that in FIG. 7 bladder 24 hangs uninflated below sole 66 of foot 12, while in FIG. 3 bladder 24 is filled with air or other fluid so that cover 20 is forced into a more rounded configuration, encircling foot 12.

Figure 8:
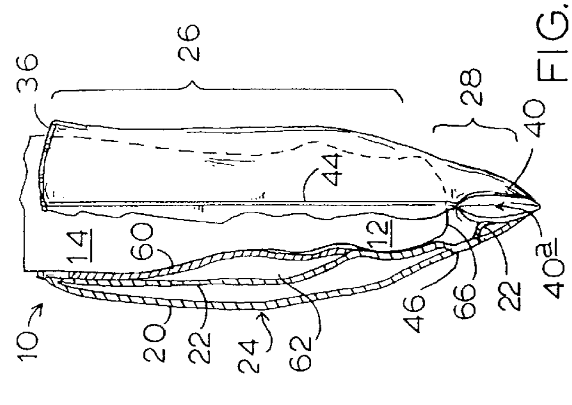
FIG. 8 is an elevation of the rear of the boot shown in FIG. 7, with the left side of the boot being fragmented generally along line 8—8 of FIG. 7.

FIG. 8 shows boot 10 in a mostly uninflated state, as in FIG. 7. It will be seen that liner 22 and thermal treatment device 62, within leg portion 26, are pressed slightly against lower leg 14, and that liner 22 within sole portion 28 hangs below sole 66 of foot 12. The open-looped aspect of the heel of boot 10, caused by independently formed heel seal 40, is indicated generally at **40*a*. The portion of liner 22 that hangs below sole 66 is the portion that forms a foot-supporting contour for sole portion 28 when bladder 24 is inflated, as seen best in FIG. 9**.

Figure 9:
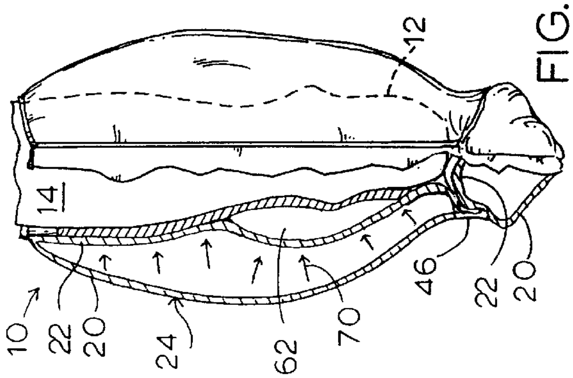
FIG. 9 is an elevation of the rear of the boot shown in FIG. 8, with the boot being shown inflated and in its relaxed condition, similar to its condition in FIGS. 1 through 4.

Also seen in FIG. 9 is the interaction between structural interconnection 46, cover 20, and liner 22. As bladder 24 is inflated, liner 22 within sole portion 28 folds up around structural interconnection 46, forming the foot-conforming contour seen in FIG. 9, as well as in FIGS. 1, 3 and 4. Pressure-indicating arrows 70 in FIG. 9 illustrate that the fluid within bladder 24 presses relatively evenly on foot 12 and lower leg 14.

Figure 10:
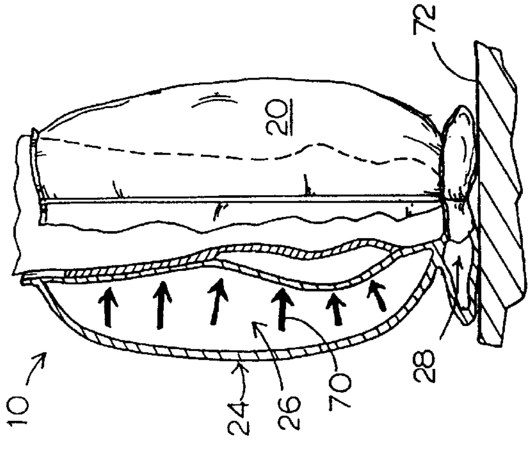
FIG. 10 is an elevation of the rear of the boot shown in FIG. 9, fragmented generally as shown in FIGS. 8 and 9, with the boot being shown in its pressurized condition, with an inserted foot pressed against a floor or other surface.

In FIG. 10, boot 10 is shown in its pressurized condition, with foot 12 having been pressed against a surface 72 to crush substantially sole portion 28. Crushing sole portion 28 significantly reduces the volume of sole portion 28, thereby increasing the fluid pressure within sole portion 28. As discussed above, a pressure increase within one portion of bladder 24 is communicated to the remaining portions of bladder 24, so that a pressure increase within sole portion 28 causes a pressure increase within leg portion 26. This pressure increase is indicated by the increased size of pressure-indicating arrows 70 in FIG. 10 compared to FIG. 9. It also will be noted that cover 20 of boot 10 is forced into a much more rounded configuration in FIG. 10, when compared to FIG. 9.

A simple pressing motion, as described in the background of this document and shown in FIG. 10, preferably controls the increase and decrease in pressure within boot 10. Alternatively, boot 10 may be attached to a pump and release valve, not shown, so that boot 10 may be pressurized and depressurized automatically. If this were the case, FIG. 10 would show sole portion 28 in a more rounded configuration, because sole portion 28 would not need to be pressed against surface 72.

FIGS. 11 through 14 illustrate the preferred steps to manufacture the preferred embodiment. Beginning with FIG. 11, pocket 60 and liner 22, both preferably made from clear or translucent polyurethane, are shown in the desired final shape. Each pocket 60 is sealed along three edges to liner 22, as indicated by dashed lines 60a. The sealing may be performed by using adhesive, or applying heat, radio frequency, or other method, as desired.

Figures 11, 12, 13, 14:
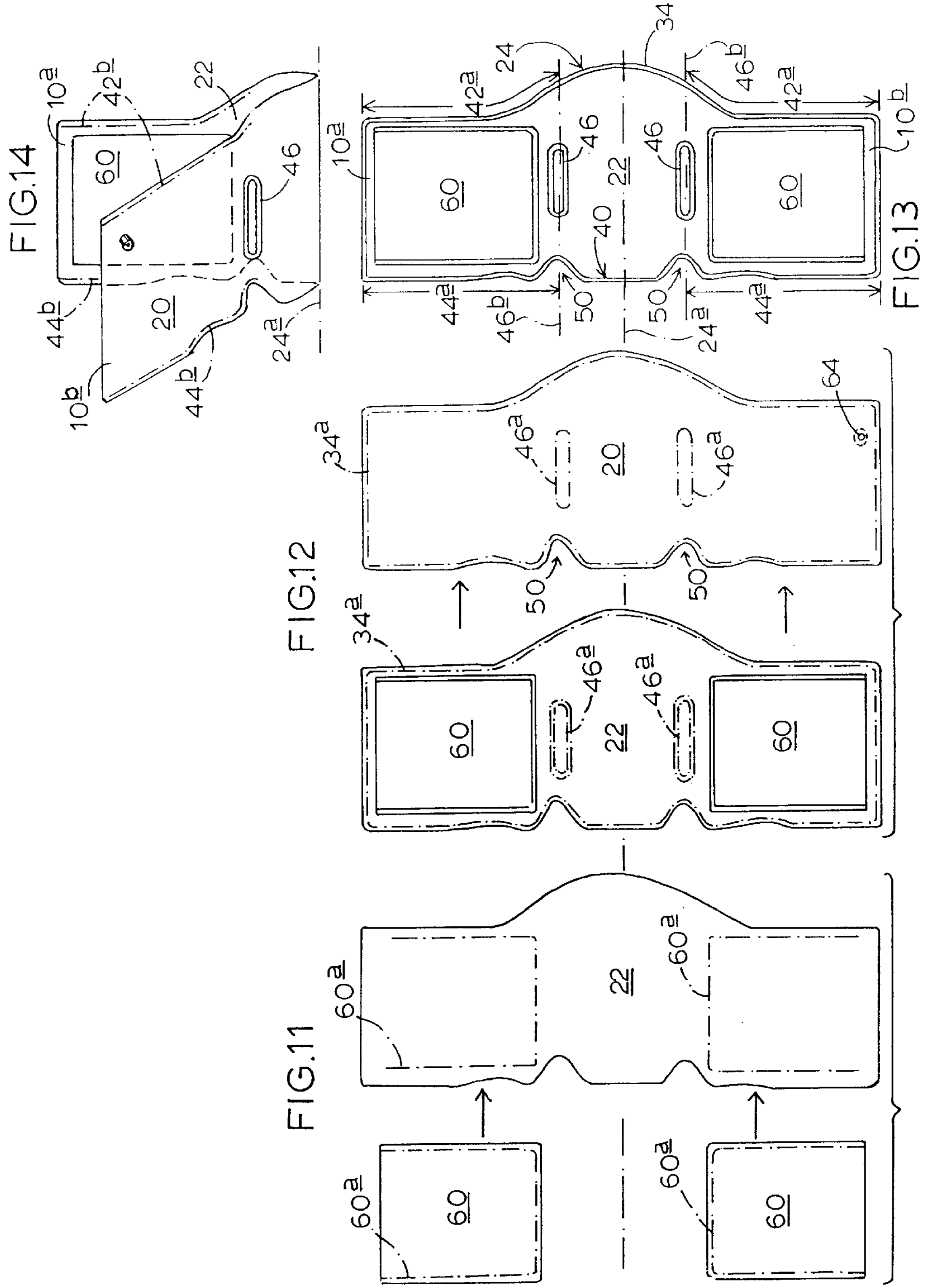
FIG. 11 illustrates the first step in the preferred method of manufacturing the boot shown in FIGS. 1 through 10, in which material that will be pockets for the boot is attached to material that will be the liner of the boot.
FIG. 12 illustrates the second step in the preferred method of manufacturing the boot, in which the pocket/liner combination from Fig. 11 is sealed to a sheet of material that will be the cover of the boot, collectively to define a bladder for the boot.
FIGS. 13 and 14 illustrate the third step in the preferred method of manufacturing the boot, in which the bladder from FIG. 12 is folded over upon itself, and joined at a seam to define an inflatable boot.

In FIG. 12, the liner/pocket combination 22/60 is shown being applied to cover 20. Cover 20 has been made from a sheet of material such as coated nylon fabric, and inlet/outlet valve 64 already has been attached to cover 20. Liner 22 then is sealed to cover 20 to form bladder seal 34, along dashed lines 34*a*. Liner 22 and cover 20 are of substantially the same size so that the sealing may be done with a simple, flat lay-up of liner 22 on cover 20. Liner 22 also is sealed to cover 20 to form structural interconnection 46, as indicated by dashed lines 46*a*. Seals 34 and 46 may be created by heat sealing, radio frequency sealing, adhesives, or other desired method.

In FIG. 13, the cover/liner/pocket combination 20/22/60 formed in FIG. 12 is shown, ready for the final step in manufacturing boot 10. The combination 20/22/60 forms bladder 24, which is folded over upon itself about a fold line 24*a* to define left side 10*a* and right side 10*b* of boot 10 relative to fold line 24*a*. In FIG. 14, bladder 24 is shown partially folded about fold line 24*a*.

Folded-over, adjacent portions of bladder seal 34 then further are joined to form front seam 42 and rear seam 44. The portions of left side 10*a* that are joined directly to matching portions of right side 10*b* are indicated in FIG. 13 by dimensional arrows 42*a* and 44*a*, and in FIG. 14 by dashed lines 42*b* and 44*b*. Seams 42 and 44 may be formed using the same methods used to form bladder seal 34 and island seal 46, as desired. It will be seen in FIGS. 13 and 14 that island seals 46 are displaced from fold line 24*a*, preferably located along an opposed pair of lines 46*b*, each of which extends through a respective notch 50 and each of which is approximately parallel to fold line 24*a*.

When rear seam 44 is completed, it preferably extends along only approximately an upper one-half of each notch 50, and extends away from fold line 24*a* along notches 50, as indicated by dimensional arrows 44*a* in FIG. 13, and dashed lines 44*b* in FIG. 14. Paired portions of seal 40 extend along approximately a lower half of notch 50, separate from seam 44 so that the paired portions of seal 40 may extend in approximately opposite directions relative to each other, approximately perpendicular to seam 44, a seen best in FIG. 9. Heel portion 40 of seal 34 forms a loop extending from seam 44 (as represented by arrows 44*a* and lines 44*b*) to fold line 24*a* and back again, as discussed above with respect to FIG. 8 (see item 40*a* in FIG. 8). Independently formed heel seal 40 operates on bladder 24 to cause bladder 24 to form fluid-filled cushions 28 and 56 under foot 12 (see FIG. 1), when foot 12 is inserted into boot 10 and bladder 24 is inflated.

The resulting construction of boot 10 may be described as liner 22 being folded over upon itself to create an inner boot for encasing a human foot when so folded, and cover 20 being folded over upon liner 22 to create an outer boot for encasing a human foot and the inner boot when so folded. Cover 20 is joined to liner 22 along continuous peripheral bladder seal 34 to define bladder 24, and further joined along front seam 42 and rear seam 44 to define portions of the inner and outer boots. This description suggests an alternative, but probably more difficult, method of manufacturing boot 10, in which boot 10 is assembled in the folded-over configuration of the final product, rather than in the prior-to-being-folded-over configuration shown in FIGS. 11 through 13.

An alternative embodiment of the inflatable boot of the present invention is shown in FIGS. 15 through 19. In this alternative embodiment, many of the elements discussed above with respect to the preferred embodiment are present. Rather than reintroducing these elements, they are identified below and in the drawings with the reference characters used above and in FIGS. 1 through 14, each preceded by a "1." Thus, the boot in FIGS. 15 through 19 is indicated generally at 110.

The structural interconnections of FIGS. 1 through 14 has been replaced by sling 174. Sling 174 may be made of any convenient flexible sheet material, such as the nylon fabric used for cover 20, or the polyurethane used for liner 22. Sling 174 is undersized relative to cover 120 and liner 122 so that sling 174 hangs substantially above cover 120 within sole portion 128, as shown in FIGS. 15 and 16 by fold line 174*a* of sling 174.

Because of this difference in size of sling 174 relative to cover 120 in liner 122, it is difficult to attach sling 174 to liner 122 during the manufacturing steps illustrated for the preferred embodiment in FIGS. 11 through 13. Accordingly, sling 174 best is attached to liner 122 after front and rear seams 142 and 144 are formed, preferably by being adhered to liner 122 with adhesive. The adhesive may be applied generally in the geometric form of lines 60*a* in FIG. 11, showing the seam in the preferred embodiment between pocket 60 and liner 22. In FIG. 15, the adhesive is indicated by line 160*a*. Alternatively, pocket 160 may be a sheet of material separate from sling 174, formed as part of the manufacturing step shown in FIG. 11, or formed on sling 174 prior to the attachment of sling 174 to liner 122.

Figure 16:
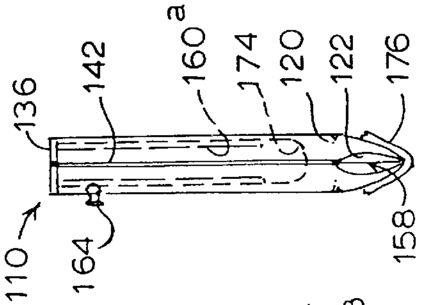
FIG. 16 is an elevation of the front of the boot shown in FIG. 15, viewed similarly to the boot shown in FIG. 6.
Figure 15:
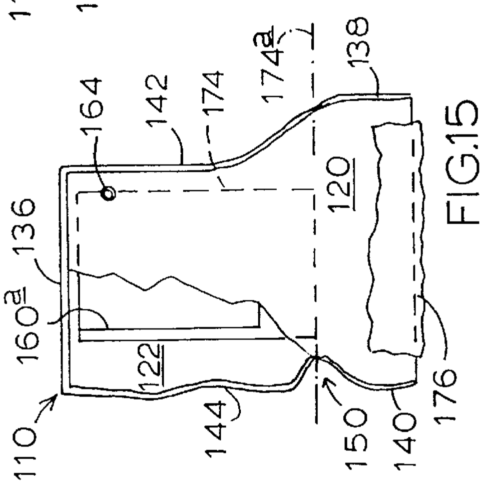
FIG. 15 is an elevation of the right side of an alternative embodiment of the boot, viewed similarly to the boot shown in FIG. 5, with the boot in FIG. 15 being fragmented to expose hidden portions of the boot.

An optional element of boot 110 is also shown in FIGS. 15 and 16, in the form of a neoprene tread 176. Tread 176 may be used with the preferred embodiment shown in Figs.1 through 14, if desired. Tread 176 increases the wear resistance of an inflatable boot, but also increases the cost and weight of the boot.

Figure 17:
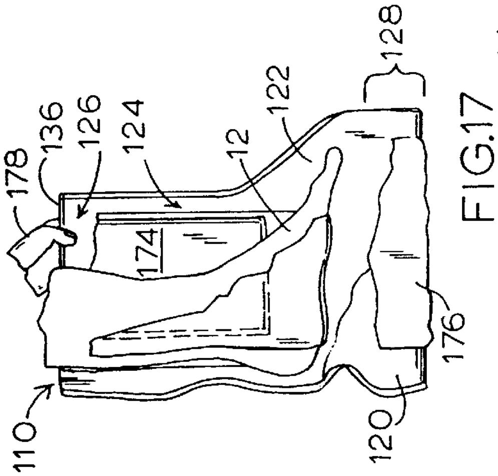
FIG. 17 is an elevation of the right side of the boot shown in FIG. 15, with the boot being further fragmented to expose additional details, and with a foot shown inserted into the boot and the boot in its uninflated condition.

Turning to FIG. 17, the operation of sling 174 is illustrated, with a foot 12 shown inserted into boot 110, while boot 110 is in its mostly uninflated condition. A wall portion 126 of boot 110 is held by a hand 178. It will be seen that foot 12 is supported by suspended sling 174 in approximately the desired final position of foot 12 within boot 110, similar to the position shown in FIG. 7. When foot 12 is inserted into bladder 124, it contacts sling 174 substantially before contacting sole portion 128. Thus, sling 174 provides a positive-positioning element for boot 110, operating as a platform-defining element suspended within bladder 124, located inwardly of inner layer 122. Foot 12 may therefore be supported by a cushion formed by sole portion 128 of bladder 124 when bladder 124 is inflated, the cushion being defined between sling 174 and cover 120. This feature may be used in connection with the embodiment illustrated in FIGS. 1 through 14, if desired, so that structural interconnection 46 operates in cooperation with sling 174.

Figure 19:
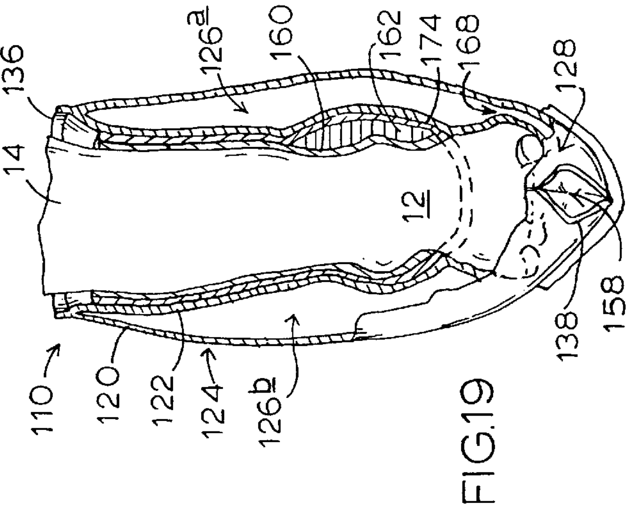
FIG. 19 is an elevation of the front of the boot shown in FIG. 17, with the boot fragmented to expose details of the sling portion of the alternative embodiment, and with the boot shown in a partially inflated condition.
Figure 18:
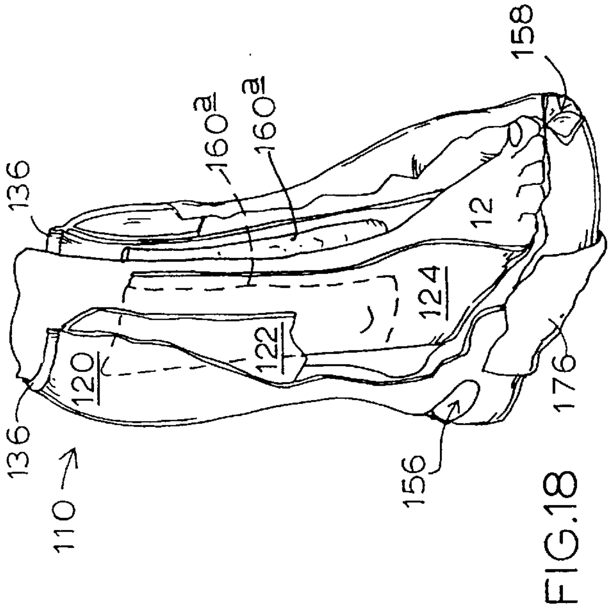
FIG. 18 is a fragmentary isometric view of the boot shown in FIG. 17, with the boot shown in a partially inflated condition, and the isometric view taken similarly to the view shown in FIG. 1.

FIGS. 18 and 19 show boot 110 with foot 12 and lower leg 14 inserted, and with boot 110 partially inflated. FIG. 18 provides a view of boot 110 similar to the view of boot 10 shown in FIG. 1. FIG. 19 provides a front view of boot 110 similar to the front view of boot 10 shown in FIG. 4. In FIG. 19, a pocket 160 is shown formed out of a separate sheet of material on sling 174.

From the foregoing identification of the elements of the preferred and alternative embodiments, numerous different embodiments may be described. Thus, while the present invention has been shown and described by reference to selected embodiments, it will be apparent to those skilled in the art that other changes in form and detail may be made therein without departing from the spirit and scope of the invention defined in the appended claims.

I claim:

1. An inflatable boot, comprising:

a bladder for encasing a human foot, including an inner layer and an outer layer of substantially gas-tight material joined by a continuous seal, and including fluidically interconnected wall and sole portions, the sole portion having a heel and a toe each said heel and toe having outer ends;

an island seal in the bladder formed by a substantially direct connection between the outer layer and the inner layer at a location on an external surface of the bladder interposed the sole portion and one of the wall portions and the heel and the toe, independent of the continuous seal said island seal having a heel end and a toe end spaced from respective outer ends of the heel and toe; and a first inflatable passageway and a second inflatable passageway fluidically interconnecting the wall portion and the sole portion between the heel end and the toe end of the island seal and respective outer ends of the sole portion.

2. An inflatable boot comprising:

a bladder for encasing at least a portion of a human foot and at least a portion of an ankle, the bladder defined by an inner and an outer layer of substantially gas-tight material, and including wall portions fluidically interconnected to a sole portion, the wall portions sized and shaped for collectively encasing a human ankle and the sole portion sized and shaped for encasing a sole of a human foot, the sole portion having a heel region and a toe region each said heel and toe region having outer ends;

a pair of spaced apart structural interconnections, each structural interconnection joining the inner layer of the bladder substantially directly to the outer layer at a location interposed the sole portion and one of the wall portions and interposed the heel region and the toe region, each said structural interconnection having a heel end and a toe end spaced from respective outer ends of the heel and toe regions each structural interconnection creating a foot-supporting contour for the sole portion of the bladder when the bladder is inflated and defining at least a first and a second passageway, the first passageway fluidically interconnecting the toe region of the sole portion substantially directly to one of the wall portions between the toe end of each structural interconnection and the outer end of the toe region and the second passageway fluidically interconnecting the heel region of the sole portion substantially directly to one of the wall portions between the heel end of each structural interconnection and the outer end of the heel region, allowing relatively unobstructed fluid flow between the sole portion and the one of the wall portions within portions within the heel region and within the toe region.

3. The inflatable boot according to claim 2, wherein:

the inner and outer layers of the bladder encompass an inflatable interior;

the bladder is folded over upon itself about a fold line and joined at a front seam and a rear seam; and the structural interconnection is intermediate the front seam and the rear seam, displaced from the fold line.

4. The inflatable boot according to claim 2, wherein:

the inner and outer layers of the bladder encompass an inflatable interior;

the bladder is folded over upon itself about a fold line to define left and right sides of the bladder relative to the fold line, and portions of the left side of the bladder are joined to matching portions of the right side to define a front seam and a rear seam;

the structural interconnection is in the left side of the bladder, intermediate the front seam and the rear seam, displaced from the fold line; and an additional structural interconnection joining the inner layer of the bladder substantially directly to the outer layer at a location interposed the sole portion and the wall portion is in the right side of the bladder, intermediate the front seam and the rear seam, displaced from the fold line.

5. The inflatable boot according to claim 2, wherein a notch is included in the periphery of the bladder to provide a visual reference indicating the proper placement of a heel of a human foot, prior to inflating the bladder, so that an inflated cushion may form properly under a sole of a foot when a heel of a foot is held approximately aligned with the notch and the bladder is inflated.

6. The inflatable boot according to claim 2, further comprising a pocket on the inner layer of material of the bladder so that a thermal treatment device may be held in the pocket, and may be sandwiched between the bladder and at least a portion of a lower leg, ankle or foot that is inserted into the bladder, when the bladder is inflated.

7. An inflatable boot comprising:

a first layer of substantially gas-tight material folded over upon itself to create an inner boot for encasing a human foot when so folded; and a second layer of substantially gas-tight material folded over upon the first layer to create an outer boot for encasing a human foot and the inner boot when so folded, the second layer joined to the first layer along a continuous seal to define a substantially gas-tight bladder;

wherein the first and second layers of material encompass an interior of the bladder; the bladder includes fluidically interconnected wall and sole portions, the sole portion including a heel region and a toe region;

the first layer is connected substantially directly to the second layer to form a structural interconnection for the bladder substantially separate from the seal, the structural interconnection operating on the bladder so that a fluid-filled cushion may be caused to form under a foot that is inserted into the inner boot, when the bladder is inflated and defining at least a first and a second passageway the first passageway fluidically interconnecting the toe region of the sole portion substantially directly to one of the wall portions and the second passageway fluidically interconnecting the heel region of the sole portion substantially directly to one of the wall portions, allowing relatively unobstructed fluid flow between the sole portion and one of the wall portions within the heel region and within the toe region.

8. The inflatable boot according to claim 7, wherein:

the first and second layers of material encompass an interior of the bladder;

the region of noninflation is a first region of noninflation; and the first layer is connected substantially directly to the second layer to form a second structural interconnection for the bladder substantially separate from the seal and the first structural interconnection.

9. The inflatable boot according to claim 7, wherein a notch is included in the periphery of the bladder to provide a visual reference indicating the proper placement of a heel of a human foot, prior to inflating the bladder, so that an inflated cushion may form properly under the sole of a foot when the heel of a foot is held approximately aligned with the notch and the bladder is inflated.

10. The inflatable boot according to claim 7, further comprising a pocket on the first layer of material of th bladder so that a thermal treatment device may be held in the pocket, and may be sandwiched between the bladder and at least a portion af a lower leg, ankle or foot that is inserted into the bladder, when the bladder is inflated.

11. A bladder for an inflatable boot, the bladder comprising:

an inflatable leg portion having an opening through which a human foot may be inserted, the leg portion defined by an inner layer of flexible material and an outer layer of material, a portion of the outer layer defining an external surface of the bladder;

an open-looped, inflatable sole portion contiguous with the leg portion, the sole portion having a toe and a heel each said toe and heel having outer ends, the sole portion being defined by the inner layer of material and the outer layer of material;

a structural interconnection connecting the inner layer substantially directly to the outer layer on the external surface of the bladder, the structural interconnection located between the leg portion and the sole portion of the bladder, and located between the toe and heel of the sole portion each said structural interconnection having a heel and a toe end spaced from respective outer ends of the toe and heel; and a first and a second passageway, the first passageway fluidically interconnecting the toe of the sole portion substantially directly to the leg portion between the toe end of the structural interconnection and the outer end of the toe and the second passageway fluidically interconnecting the heel of the sole portion substantially directly to the leg portion between the heel end of the structural interconnection and the outer end of the heel, allowing relatively unobstructed fluid flow between the sole portion and the leg portion within the heel region and within the toe region.

12. The bladder according to claim 11, wherein:

the inner and outer layers of material encompass an interior of the leg portion and sole portion;

the structural interconnection is a first structural interconnection; and the inner layer is connected substantially directly to the outer layer to form a second structural interconnection substantially separate from the first structural interconnection.

13. The inflatable boot according to claim 11, wherein a notch is included in the periphery of the bladder to provide a visual reference indicating the proper placement of a heel of a human foot, prior to inflating the bladder, so that an inflated cushion may properly form under the sole of a foot when the heel of a foot is held approximately aligned with the notch and the bladder is inflated.

14. The inflatable boot according to claim 11, further comprising a pocket on the inner layer of material of the bladder so that a thermal treatment device may be held in the pocket, and may be sandwiched between the bladder and at least a portion of a lower leg, ankle or foot that is inserted into the bladder, when the bladder is inflated.

15. An inflatable boot comprising:

a first layer of substantially gas-tight material folded over upon itself to create an inner boot for encasing a human foot when so folded; and a second layer of substantially gas-tight material folded over upon the first layer to create an outer boot for encasing a human foot and the inner boot when so folded, the second layer joined to the first layer along a continuous peripheral seal to define a substantially gas-tight bladder, at least two folded-over, adjacent portions of the bladder substantially directly interconnected to form a seam defining a portion of the inner and outer boots;

wherein the folding over of the first and second layers defines a fold line;

the first and second layers include a substantial inwardly extending notch along a portion of the seal and including an end of the seam;

the seam extends along only approximately an upper one-half of the notch;

paired portions of the seal extend along approximately a lower half of the notch, separate from the seam so that the paired portions of the seal may extend in approximately opposite directions relative to each other, approximately perpendicular to the seam; and a portion of the seal forms a loop extending from the seam to the fold line and back again, the loop allowing the bladder to expand outwardly to form a fluid-filled cushion under a foot that is inserted into the inner boot, when the bladder is inflated.

16. The inflatable boot according to claim 15, wherein:

the first and second layers of material encompass an interior of the bladder;

the first layer is connected substantially directly to the second layer to form a region of noninflation for the bladder substantially separate from the notch, located along a line that extends through the notch and is approximately parallel to the fold line.

17. The inflatable boot according to claim 16, wherein the region of noninflation for the bladder is substantially separate from the seal.

18. The inflatable boot according to claim 16, wherein:

the region of noninflation is a first region of noninflation;

the first layer is connected substantially directly to the second layer to form a second region of noninflation for the bladder substantially separate from the seal and the first region of noninflation.

19. The inflatable boot according to claim 15, further comprising a pocket on the first layer of material of the bladder so that a thermal treatment device may be held in the pocket, and may be sandwiched between the bladder and at least a portion of a lower leg, ankle or foot that is inserted into the bladder, when the bladder is inflated.

20. An inflatable boot comprising:

a bladder for encasing a human foot, the bladder defined by an inner and an outer layer of substantially gas-tight material, the inner layer being substantially the same size as the outer layer, and the bladder including fluidically interconnected wall and sole portions, the wall portions sized and shaped for collectively encasing a human leg and the sole portion for encasing the bottom of a human foot; and a platform-defining sling suspended within the bladder, the sling including a pair of elongate sides connecting a heel region and a toe region of the sling, each elongate side of the sling being attached to the inner layer interposed a respective wall portion and the sole portion, and being located inwardly of the inner layer of the bladder so that a human foot that is inserted into the bladder may be supported by the sling when the bladder is uninflated and held by the wall portions, and so that a human foot that is inserted into the bladder may be supported by a cushion formed by the sole portion of the bladder when the bladder is inflated, the cushion defined between the sling and the outer layer.

21. The inflatable boot according to claim 20, further comprising a structural interconnection joining the inner layer of the bladder substantially directly to the outer layer at a location interposed the sole portion and one of the wall portions, the structural interconnection, in cooperation with the sling, creating a foot-supporting contour for the sole portion of the bladder when the bladder is inflated.

22. The inflatable boot according to claim 20, further comprising a pocket included on the bladder so that a thermal treatment device may be held in the pocket, the pocket oriented so that a thermal treatment device may be sandwiched between the bladder and at least a portion of a lower leg, ankle or foot that is inserted into the bladder, when the bladder is inflated.

* * * * *